(12) United States Patent
Hollander et al.

(10) Patent No.: US 6,319,005 B1
(45) Date of Patent: Nov. 20, 2001

(54) DENTAL IRRIGATION DRILL WITH INTERNAL ANTI-BACKWASH BAFFLE

(75) Inventors: Bruce Hollander; Ingo Kozak, both of Boca Raton, FL (US)

(73) Assignee: BioLok International Inc., Deerfield Beach, FL (US)

( * ) Notice: Subject to any disclaimer, the term of this patent is extended or adjusted under 35 U.S.C. 154(b) by 0 days.

(21) Appl. No.: 09/664,548

(22) Filed: Sep. 18, 2000

(51) Int. Cl.[7] .................................................. A61C 3/02
(52) U.S. Cl. ............................................. 433/165; 408/59
(58) Field of Search ................................... 433/165, 166; 408/59, 205

(56) References Cited

U.S. PATENT DOCUMENTS

| | | | | |
|---|---|---|---|---|
| 4,021,920 | * | 5/1977 | Kirschner et al. | 433/165 |
| 4,127,279 | * | 11/1978 | Wright | 408/59 |
| 5,261,818 | * | 11/1993 | Shaw | 433/165 |
| 5,569,035 | * | 10/1996 | Balfour et al. | 433/165 |
| 5,791,902 | * | 8/1998 | Lauks | 433/165 |
| 5,839,897 | * | 11/1998 | Bordes | 433/165 |

* cited by examiner

Primary Examiner—Nicholas D. Lucchesi
(74) Attorney, Agent, or Firm—M. K. Silverman

(57) ABSTRACT

A dental drill, formed of a substantially solid elongate body, includes (a) a longitudinal shank having a proximal and a distal end and having an axially disposed irrigation channel; (b) a working portion comprising (i) an annular boss integrally disposed distally of the shank; (ii) a neck of reduced radius relative to the boss, integrally disposed distally of the boss; (iii) a cutting region of uniform diameter integrally disposed distally of the neck; and (iv) a cutting region having a tapered external geometry, integrally dependant distally of the cutting region of uniform diameter, the cutting regions including at least four integral axi-symmetric flutes formed upon lateral surfaces of the regions, each of the flutes defining co-axial peripheral profiles, each of the flutes separated by substantially co-axial integral channels, each having at least one outlet therein, the working portion of the drill having an irrigation channel extending the entire length and integral with the shank irrigation, the one outlet of each axial channel located proximally to a distal tip of the tapered cutting region, the tip defining a surface formed integrally and continuously with distal ends of the flutes and channels; and (c) a fluid-tight unidirectional baffle formed between opposing complemental surfaces of the shank and working portions, inclusive of the irrigation channels thereof, the baffle defining a one-way interior valve situated at an interface of the irrigation channels to preclude proximal fluid backflow within the irrigation channel of the shank during use of the dental drill.

9 Claims, 2 Drawing Sheets

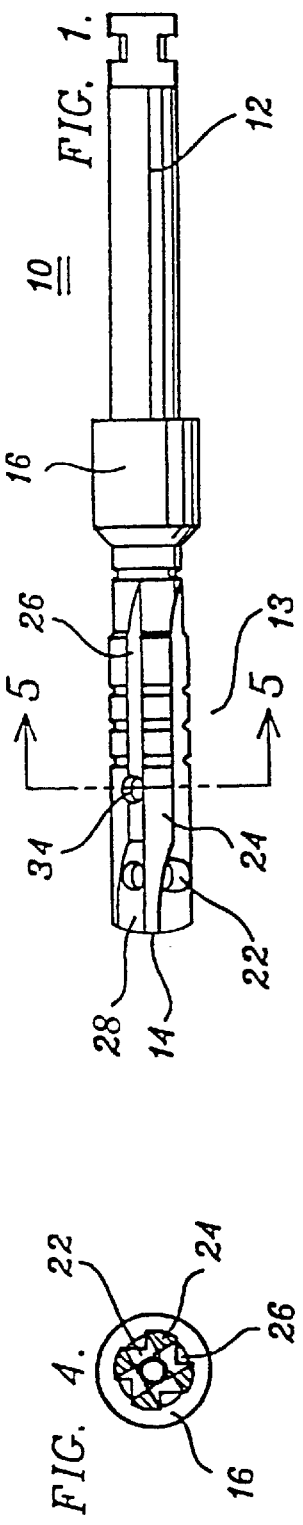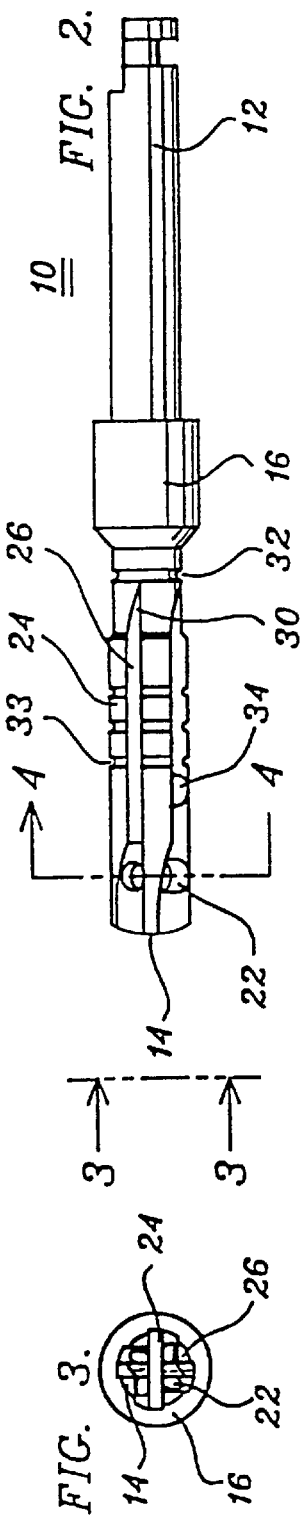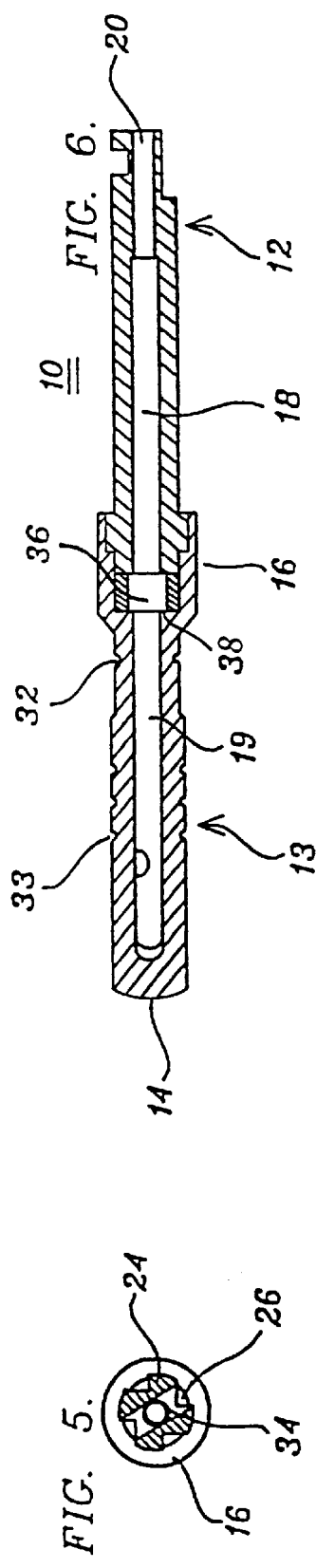

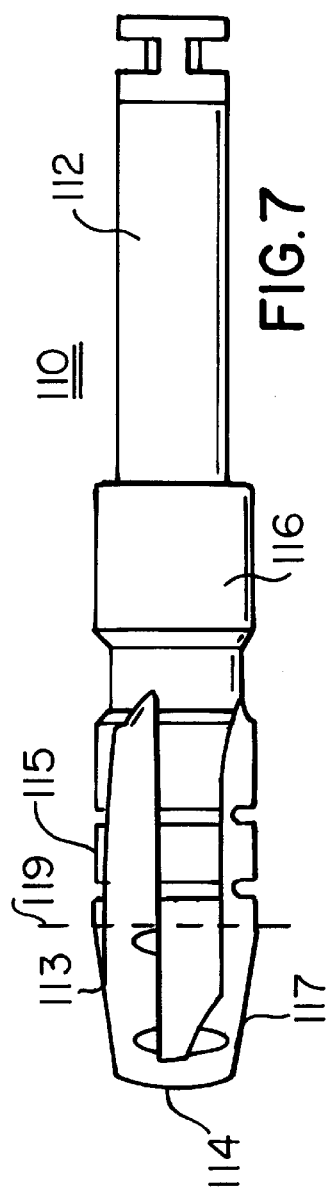
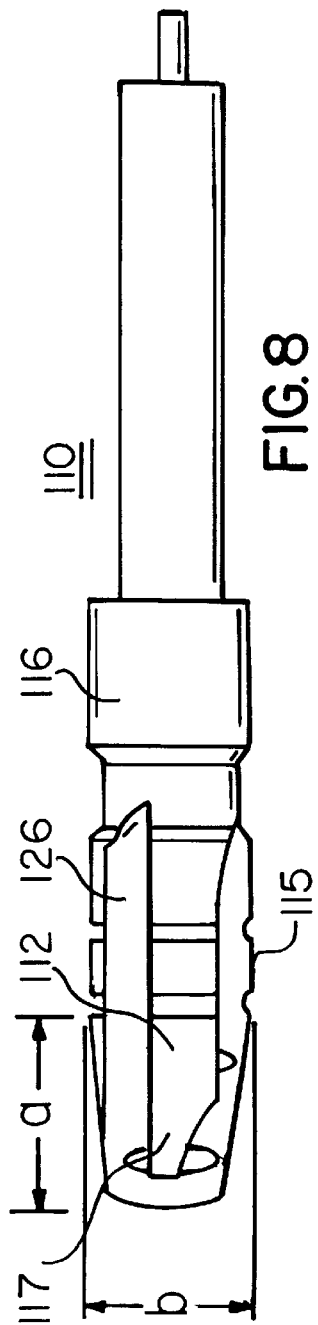
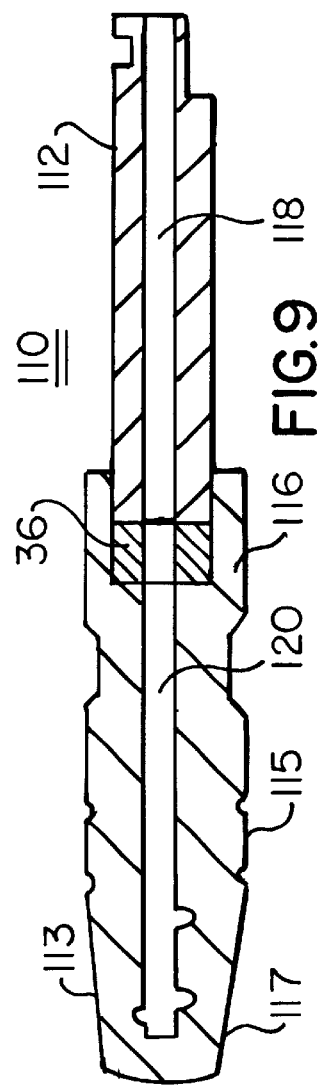

DENTAL IRRIGATION DRILL WITH INTERNAL ANTI-BACKWASH BAFFLE

BACKGROUND OF THE INVENTION

The present invention is an improvement of the invention of U.S. Pat. No. 5,261,818 (1993) to Shaw, entitled Multi-Fluted Dental Irrigation Drill, and U.S. Pat. No. 6,106,292 (2000) to the present inventive entity, entitled Dental Irrigation Drill with Internal Anti-Backwash Baffle.

The invention relates to dental drills and, more particularly, to so-called fluted irrigation spade drills employed in the creation of channels in the human jaw prior to the insertion of an implant of a post upon which a dental structure such as an abutment or bridge is to be placed. A difficulty in prior art dental drills of the above type is that, due to rotational eccentricity and flutter relative to the axis of rotation of the drill, a degree of trauma is imparted to the jawbone of the patient. Further, the dentist cannot effectively control pressure and depth of penetration of the drill where eccentricity or flutter exists in the drill action.

The present improvement of the above-referenced patent to Shaw entails changes in the external geometry thereof and, internally, provides to the irrigation channel thereof an anti-backwash baffle formed between opposing press-fittable complemental surfaces of a shank cutting portion of the drill. Accordingly, the present invention improves upon the invention of Shaw both in terms of cutting effect of external geometry and in terms of internal fluid flow characteristic. More particularly, the structure of the present invention employs a flat stub nose geometry, as opposed to complex distal end surfaces of the drill of Shaw and, additionally, provides an internal baffle or valve to create a fluid tight seal medially within the irrigation channel of the drill to prevent backwash into the shank portion thereof, a phenomenon which is undesirable in terms of both the aesthetics of implant dentistry and in terms of disrupting concentration of the dentist during implant procedures. These advantages are achieved while maintaining the positive associated with said reference to Shaw, namely, a superior implant cutting tool which facilitates a maximum of osseo-integratation of the implant within the implant site of the jawbone.

Other related art known to the within inventors includes U.S. Pat. No. 5,569,035 (1996) to Balfour et al; U.S. Pat. No. 5,791,902 (1998) to Lauks; and No. U.S. Pat. No. 5,839,897 to Borders.

SUMMARY OF THE INVENTION

A dental drill, formed of a substantially solid elongate body, having: (a) a longitudinal shank including a proximal and a distal end and having an axially disposed irrigation channel; (b) a working portion comprising (i) an annular boss integrally disposed distally of said shank; (ii) a neck of reduced radius relative to said boss, integrally disposed distally of said boss; (iii) a cutting region of uniform diameter integrally disposed distally of said neck; and (iv) a cutting region having a tapered external geometry, integrally dependant distally of said cutting region of uniform diameter, said cutting regions integrally including at least four integral axi-symmetric flutes formed upon lateral surfaces of said regions, each of said flutes defining co-axial peripheral profiles, each of said flutes separated by substantially co-axial integral channels, each having at least one outlet therein, said working portion of said drill having an irrigation channel extending the entire length thereof and in integral communication with said shank irrigation, said one outlet of each axial channel located proximally to a distal tip of said tapered cutting region, said tip defining a surface formed integrally and continuously with distal ends of said flutes and channels; and (c) a fluid-tight unidirectional baffle formed between opposing complemental surfaces of said shank and working portions, inclusive of said irrigation channels thereof, said baffle defining a one-way interior valve situated at an interface of said irrigation channels to thereby preclude proximal fluid backflow within said irrigation channel of said shank during use of the dental drill.

It is an object of the present invention to provide a multi-fluted dental irrigation drill in which fluid backwash within the shank irrigation channel thereof is minimized during an implant procedure.

It is another object to provide an irrigation drill of the above type having an exterior geometry of improved cutting effectiveness relative to that known in the art.

It is a further object of the invention to provide an improved irrigation drill having particular utility in creating a bore of a depth and geometry in jaw bones, at a site of dental implant insertion, that is precisely complemental to tapered implants to be inserted into said site.

It is another object to provide a drill of the above type that will minimize the eccentricity and flutter in the rotation thereof, thusly minimizing trauma to the jaw of the patient during insertion of an implant.

It is a further object to provide an irrigation dental spade drill to enable improve control of pressure, depth and refinement of penetration by the implant dentist.

The above and yet other objects and advantages of the invention will become apparent from the hereinafter set forth Brief Description of the Drawings, Detailed Description of the Invention and Claims appended herewith.

BRIEF DESCRIPTION OF THE DRAWINGS

FIG. 1 is an axial elevational view of the inventive dental drill.

FIG. 2 is an elevational view of the drill axially rotated ninety degrees from the view of FIG. 1.

FIG. 3 is a left plan view of the drill taken along Line 3—3 of FIG. 2.

FIG. 4 is a radial cross sectional view taken along Line 4—4 of FIG. 2.

FIG. 5 is a radial cross-sectional view taken Line 5—5 of FIG. 1.

FIG. 6 is an axial cross-sectional view of FIG. 2.

FIG. 7 is an axial elevational view of a preferred embodiment of the inventive dental drill.

FIG. 8 is an axial elevational view of the drill of FIG. 7 rotated ninety degrees therefrom.

FIG. 9 is an axial cross-sectional view of the drill of FIG. 7.

DETAILED DESCRIPTION OF THE INVENTION

With reference to the views of FIGS. 1, 2, and 6, the inventive irrigation drill may be seen to comprise a substantially solid cylindrical body 10 having a proximal gripping shank 12 and working or cutting portion 13 having a distal working tip 14. Located somewhat in the middle of cylindrical body 10 at the distal end of shank 12 is an annular boss 16. Running the entire axial length of the drill is an irrigation channel, having parts 18 and 19, input 20 and a plurality of outlets 22 proximally of said tip 14. As may be particularly noted in the views of FIGS. 1 and 3, there are, formed within the lateral surface of the cylindrical body 10, at least four flutes 24 that are disposed axi-symmetrically about the axis of working portion 13. It is noted that each flute 24 defines an axial profile that is substantially co-axial with said irrigation channel 19. Further, each flute 24 is separated from its neighboring flute by substantially co-axial channels 26 that extend from said boss 16 to the area of said irrigation channel outlets 22 which each flute narrows somewhat. As noted in FIGS. 1 and 2, each channel 26 flares to a larger polar dimension at distal end 28, and tend to fishtail away from the axis of the irrigation channel at the opposite end 30 thereof.

It is to be appreciated that the pitch of the lines of interface between flutes 24 and bores 26, which exist particularly at opposite ends of working portion 13 may be manufactured in either a clockwise or counterclockwise manner to produce either left-hand or right-hand cutting capabilities, as may be desired by the individual practitioner.

It has been determined that through the use of four or more such axi-symmetric flutes 24, eccentricity, that is wiggle and flutter of the drill during use is markedly reduced, while control by the dentist is improved.

The peculiar radial cross-sectional and tip geometry of the drill may be seen with reference to the views of FIGS. 3, 4 and 5. More particularly, in FIG. 4 is shown the location of irrigation channel outlets 22 in each channel 26. In FIG. 5 is shown the location of irrigation outlets 34 in alternating channels.

As a further advantageous feature of the instant invention there are provided a plurality of serrations 32, the distal-most of which, namely, serration 33 begins at about eight millimeters from tip 14 followed, at separations of two millimeters, with successive serrations. The serrations are circumferential grooves extending about the lateral surface of the working portion 13 between outlets 34 and boss 16. Through the use of such serrations, the depth of penetration of the drill can be readily controlled by the dental practitioner.

The radial depth of each channel 26 will be between one-tenth and one-quarter of the overall diameter of the drill which is typically 2 to 7 millimeters. The entire length of drill is typically about 20 to 25 millimeters.

It is particularly noted that the improvement of the invention includes a fluid-tight unidirectional baffle 36 (See FIG. 6), in the nature of a valve, which is manufactured as an element discreet from shank 12 and working portion 13 in which, upon assembly, said baffle 36 is seated against a surface 38 within the interior geometry of working portion 13. As such, baffle 36, as seated at a surface of complemental interface between the interior geometries of shank 12 and portion 13, to define a unidirectional interior valve situated within the irrigation channels 18/19 of the drill. The function of baffle 36 is to preclude undesired proximal backflow of fluids during an implant procedure which would otherwise attempt to exit through input 20 of shank 12, thereby disrupting the implant procedure and detracting from the sanitary condition of the work site.

A preferred embodiment of the instant invention is shown in the views of FIGS. 7 through 9. This embodiment of the invention differs from the embodiment of FIGS. 1 through 6 principally in the wider exterior envelope and tapered end thereof wherein a cutting region 113 includes a substantially cylindrical subregion 115 and a subregion 117 which defines a taper in the direction of tip 114 of the cutting region. A plane of dependency 119 indicates the beginning of tapered subregion 117. The resultant geometry is, therefore, one in which tip 114 is curved and, typically, would have diameter of 2.3 millimeters relative to a diameter (dimension "b") of about 4 to about 7 millimeters of boss 116 of the entire irrigation drill 110. Dimension "a" of tapered subregion 117 is typically 6 millimeters, so that the ratio of dimension "b" to "a" relates to the sine of an angle in a range of between 4 to 15 degrees, this defining the envelope of cutting region 113.

It is noted that co-axial channels 126 of the embodiment of FIGS. 7 through 9 define a ratio of radial depth to the entire drill diameter of between 0.1 to 0.25. The embodiment of FIGS. 7 through 9 is of particular value in the creation and finishing of an implant site intended for use with a self-tapping tapered buttress thread implant, known in the art as the SILHOUETTE or tapered implant.

FIG. 9 shows the use of said backflow prevention baffle 36 at a complemental interface between interior irrigation channels 118 and 120 and opposing surfaces of shank 112 and boss 116 respectively.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

We claim:
1. A dental drill formed of a substantially solid elongate body, the drill comprising:
   (a) a longitudinal shank having a proximal end and a distal end and having an axially disposed irrigation channel;
   (b) a working portion comprising:
      (i) an annular boss integrally disposed distally of said shank;
      (ii) a neck of reduced radius relative to said boss, integrally disposed distally of said boss;
      (iii) a cutting region of uniform diameter integrally disposed distally of said neck; and
      (iv) a cutting region having a tapered external geometry, integrally dependant distally of said cutting region of uniform diameter, said cutting regions integrally including at least four integral axi-symmetric flutes formed upon lateral surfaces of said regions, each of said flutes defining co-axial peripheral profiles, each of said flutes separated by substantially co-axial integral channels, each having at least one outlet therein, said working portion of said drill having an irrigation channel extending the entire length thereof and in integral communication with said shank irrigation channel, said one outlet of each axial channel located proximally to a distal tip of said tapered cutting region, said tip defining a surface formed integrally and continuously with distal ends of said flutes and channels; and
   (c) a fluid-tight unidirectional baffle formed between opposing complemental surfaces of said shank and working portion, inclusive of said irrigation channels thereof, said baffle defining a one-way interior valve situated at an interface of said irrigation channels to thereby preclude proximal fluid backflow within said channel of said shank during use of the dental drill.

2. The dental drill as recited in claim 1 in which said shank comprises an element manufactured apart from said working portion in which said fluid-tight baffle comprises a permanent complemental press-fit contact therebetween.

3. The dental drill as recited in claim 2 in which, proximally to said tip of said tapered cutting region, the polar dimension of said channels increases as the polar dimension of said flutes decreases.

4. The dental drill as recited in claim 1 in which said tapered cutting region defines a taper relative to said uniform cutting region in a direction of said tip having an included acute angle in a range of about 4 to about 15 degrees.

5. The dental drill as recited in claim 4 in which a length from said tapered region to said tip is about 6 mm.

6. The dental drill as recited in claim 4 in which said shank comprises an element manufactured apart from said working portion in which said fluid-tight baffle comprises a permanent complemental press-fit contact therebetween.

7. The dental drill as recited in claim 6 in which, proximally to said tip of said tapered cutting region, the polar dimension of said channels increases as the polar dimension of said flutes decreases.

8. The dental drill as recited in claim 4 in which said co-axial channels between said flutes defines a radial depth of between 0.1 and 0.25 of the diameter of the cutting region of the working portion of the drill.

9. The dental drill as recited in claim 4 in which said distal tip is curved.

* * * * *